United States Patent
Shoji

(10) Patent No.: US 6,433,341 B1
(45) Date of Patent: Aug. 13, 2002

(54) METHOD AND APPARATUS FOR PHOTOGRAPHING RADIATION IMAGE AND CASSETTE FOR RADIATION DETECTION

(75) Inventor: Takashi Shoji, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/492,330

(22) Filed: Jan. 27, 2000

(30) Foreign Application Priority Data

Jan. 27, 1999 (JP) ............................................. 11-018687

(51) Int. Cl.[7] ................................................. G01T 1/24
(52) U.S. Cl. .................. 250/370.09; 250/363; 250/367; 250/370.11; 250/385.1
(58) Field of Search ............................ 350/370.09, 363, 350/367, 370.11, 385.1

(56) References Cited

U.S. PATENT DOCUMENTS

| | | | |
|---|---|---|---|
| 4,803,359 A | 2/1989 | Hosoi et al. ................. | 250/237 |
| 5,187,369 A | 2/1993 | Kingsley et al. ............ | 250/370 |
| 5,465,284 A | * 11/1995 | Karellas ................. | 250/370.09 |
| 5,661,309 A | 8/1997 | Jeromin et al. | |
| 5,773,839 A | 6/1998 | Krepel et al. | |

FOREIGN PATENT DOCUMENTS

| | | |
|---|---|---|
| JP | 1-216290 | 8/1989 |
| JP | 2-164067 | 6/1990 |
| JP | 7-140255 | 6/1995 |
| JP | 10-232824 | 2/1998 |
| JP | 10-271374 | 9/1998 |

OTHER PUBLICATIONS

"SPIE vol. 1443", Medical Imaging V: Image Physics (1991) pp. 108–119.
"Material Parameters in Thick Hydrogenated Amorphous Silicon Radiation Detectors", Lawrence Berkley Laboratory, University of California.
"Metal/Amorphous Silicon Multilayer Radiation Detectors", IEEE Transactions on Nuclear Science, vol. 36, No. 2, Apr. 1989, Yujiro Naruse and Tamotsu Hatayama.

* cited by examiner

Primary Examiner—Constantine Hannaher
Assistant Examiner—Andrew Israel
(74) Attorney, Agent, or Firm—Sughrue Mion, PLLC

(57) ABSTRACT

In a radiation image photographing apparatus using a radiation detection cassette containing an image memory, image data read from the image memory are properly related to a photographing menu used at the time of obtaining the image data. A counter value C of a photographing counter 57 in a cassette 50 is converted to radio data C' and transferred to a display apparatus 21 while being stored in an image memory 45 as accompanying information of image data D. The display apparatus 21 relates the transferred counter value C to a photographing menu. When the image data D are read from the image memory 45, the counter value C is also read and the photographing menu corresponding to the image data D is identified by referring to the counter value C.

20 Claims, 7 Drawing Sheets

F I G . 3
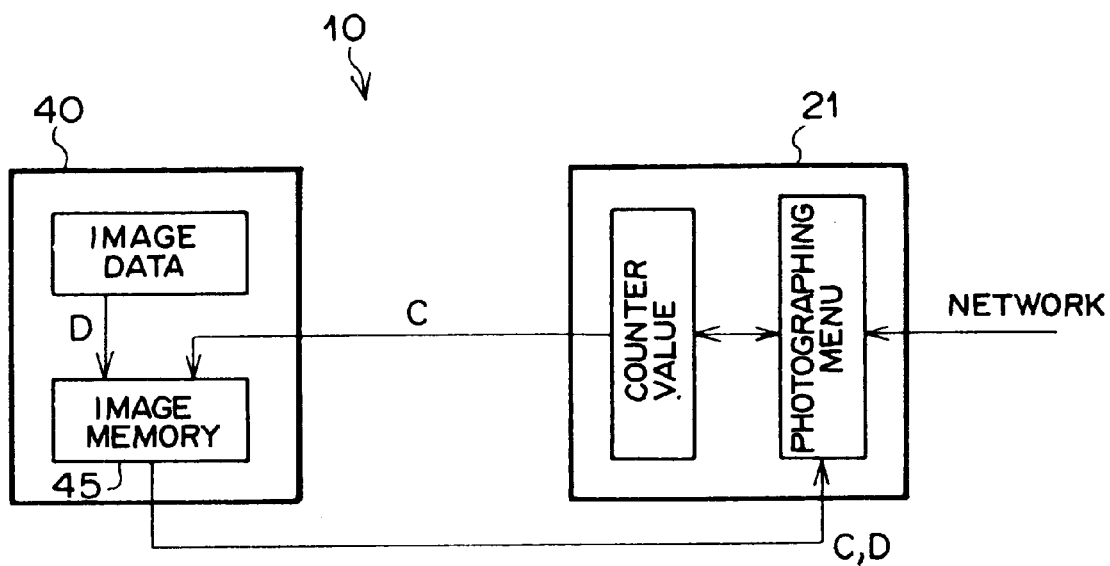

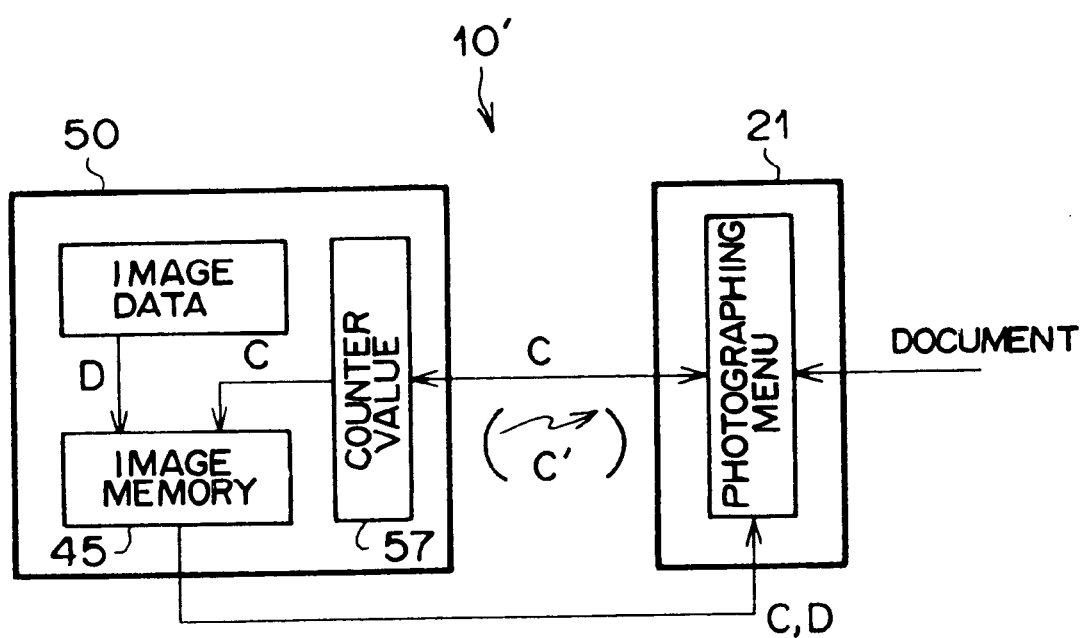
F I G. 7

METHOD AND APPARATUS FOR PHOTOGRAPHING RADIATION IMAGE AND CASSETTE FOR RADIATION DETECTION

BACKGROUND OF THE INVENTION

1. Field of the Invention

The present invention relates to a method and an apparatus for photographing radiation images by using a radiation detection cassette comprising an image memory and a solid-state radiation detector, and also to the radiation detection cassette used therefor.

2. Description of the Related Art

In today's radiography aimed at medical diagnoses or the like, radiation image photographing apparatuses using solid-state radiation detectors (whose main part comprises semiconductors; hereinafter, simply called a "detector" or a "radiation detector" in some cases) for outputting an image signal by detecting radiation have been known. As the solid-state radiation detectors used therein, various types have been proposed and put into practice.

With respect to an electric charge generating process in which radiation is converted into an electric charge, solid-state radiation detectors of different types, such as optical conversion type detectors (see Japanese Unexamined Patent Publication Nos. 59(1984)-211263 and 2(1990)-164067, PCT International Publication No. WO92/06501, and SPIE Vol. 1443 Medical Imaging V; Image Physics (1991), p. 108–119, for example) and direct conversion type detectors (MATERIAL PARAMETERS IN THICK HYDROGENATED AMORPHOUS SILICON RADIATION DETECTORS, Lawrence Berkeley Laboratory, University of California, Berkeley, Calif. 94720 Xerox Parc. Palo Alto, Calif. 94304, Metal/Amorphous Silicon Multilayer Radiation Detectors, IEEE TRANSACTIONS ON NUCLEAR SCIENCE. VOL. 36. NO.2. APRIL 1989, and Japanese Unexamined Patent Publication No. 1(1989)-216290, for example), have been known. In an optical conversion type detector, light emitted from a phosphor by exposing the phosphor to radiation is detected by a photoelectric conversion device and a signal charge thereby obtained is stored in a capacitor of the device. The stored electric charge is then converted into an image signal (electrical signal) and the signal is output. In a direct conversion type detector, a signal charge generated within a radiation conductive material by exposing the material to radiation is collected by an electric charge collecting electrode and stored in a capacitor. The stored electric charge is then converted into an electrical signal and the signal is output.

With respect to an electric charge reading process in which a stored electric charge is read out, solid-state radiation detectors of other types, such as TFT reading type detectors which read the charge by scanning TFT's (Thin Film Transistors) connected to capacitors and optical reading type detectors in which a charge is read by irradiation of reading light (an electromagnetic wave for reading) thereon have been known.

The present assignee has proposed radiation detectors of improved direct conversion type (see Japanese Patent Application Nos. 10(1998)-232824 and 10(1998)-271374). A radiation detector of improved direct conversion type means a radiation detector employing both the direct conversion method and the optical reading method. The radiation detector of improved direct conversion type comprises a first conductive layer which is transparent to radiation for recording, a photoconductive layer for recording exhibiting photoconductivity (or radiation conductivity, more accurately) when receiving the radiation for recording which has passed through the first conductive layer, an electric charge transport layer which acts as an insulator to an electric charge having the same polarity as the electric charge charged in the first conductive layer while acting as a conductor to an electric charge having the reversed polarity, a photoconductive layer for reading presenting photoconductivity (or more accurately, electromagnetic wave conductivity) by receiving an electromagnetic wave for reading, and a second conductive layer which is transparent to the electromagnetic wave for reading, with these layers being stacked in this order. A signal electric charge (latent image electric charge) representing image information is stored at the interface (the capacitor) between the photoconductive layer for recording and the electric charge transport layer. The first and the second conductive layers function as electrodes. The photoconductive layer for recording, the electric charge transport layer, and the photoconductive layer for reading comprise the main part of the solid state detector of this type.

Various kinds of cassette for radiation detection containing in a case a radiation detector and an image memory as recording means for recording an image signal output from the detector have been proposed (for example, see U.S. Pat. Nos. 5661309 and 5773839, and Japanese Unexamined Patent Publication Nos. 6(1994)-342099 and 7(1995)-140255). The cassette described in U.S. Pat. No. 5661309 uses an image memory having a recording capacity for a plurality of images, and stores image data for one image in the image memory each time the image has been detected.

A radiation image photographing apparatus using this cassette records image data for a plurality of images obtained by successive photographing in the image memory, and reads the data of the images from the image memory to collectively output the image data to a signal processing unit located outside the cassette. In this way, it becomes unnecessary to output (transfer) the image data to the external signal processing unit each time one image is detected (photographed). Therefore, efficient successive photographing becomes possible, and processing time between signal detection and signal processing can be reduced.

Meanwhile, upon photographing a radiation image, a photographer generally carries out photographing in an order determined based on a photographing menu such as patient information and photographing information displayed on an image/information display apparatus (hereinafter, simply called display apparatus) controlling photographing.

In the case where the cassette containing the image memory having recording capacity for a plurality of images is used for photographing, the image data read from the image memory do not correspond to the photographing menu used at the time of obtaining the image data, if photographing is carried out in an order different from the order determined in advance, (that is, if the order of photographing is changed during the successive photographing) and if there is no means for relating the photographing menu and the actual images represented by the image data in the image memory. Therefore, appropriate diagnoses cannot be carried out.

For example, in the case of mass medical examination of people's chests, it is common practice for subjects to be related to a photographing order in advance and a number of plate indicating the order is provided to each subject. A photographer carries out photographing in accordance with the number plates. If photographing is carried out according to the number plates, the photographed images can be related to the subjects. Otherwise, the photographed images do not correspond to the subjects, which causes a problem on diagnosis. The same problem occurs if the cassette to be used is misplaced.

Furthermore, in the field of recent medical diagnosis, networking has been in progress. A work flow is determined based on a diagnosis of a clinician, and the work flow is transferred to each consulting room via a network. Various kinds of processing are then carried out based on the work flow. A photographing menu is included in the work flow. However, processing may be carried out in a flow different from the work flow, due to convenience of a consulting room. Therefore, the likelihood of carrying out processing procedures different from the predetermined processing procedures is growing.

Therefore, realization of means for properly relating a photographing menu to image data recorded in an image memory has been desired so that no problem occurs even when a procedure different from a predetermined work flow is taken in a network environment.

SUMMARY OF THE INVENTION

The present invention has been conceived based on consideration of the above problems. An object of the present invention is to provide a radiation image photographing method and a radiation image photographing apparatus for recording radiation image data representing radiation images in an image memory in a cassette in such a manner that the image data read from the image memory can be related to a photographing menu used at the time of photographing the images, and also a cassette for radiation detection used therefor.

A radiation image photographing method of the present invention uses a radiation detection cassette containing a radiation detector for outputting image data by detecting radiation representing radiation image information obtained by photographing and an image memory for storing the image data output from the radiation detector, and the radiation image photographing method comprises the step of:

storing the image data representing images in the image memory by relating the image data of each image with a photographing menu used at the time of obtaining the image data, via a counter value for counting how many times photographing has been carried out.

The "photographing menu" herein referred to means various conditions affecting a relationship between a radiation dose at the time of photographing and the values of the image data output from the detector. As the photographing menu, a photographing mode (such as normal photographing, enlargement photographing, and tomography), a photographing condition (such as the kind of subject, a tube voltage of an X-ray source, and the radiation dose), a body part to be photographed (such as the head, neck, chest, and abdomen), and a photographing apparatus can be listed. Hereinafter, these conditions are collectively called a photographing menu.

The "counter value for counting how many times photographing has been carried out" can be numbers such as 1, 2, and 3 but also characters or symbols such as A, B, and C, as long as the order of photographing can be. managed thereby. The counter for obtaining the counter value can be located anywhere as long as the counter can manage the order of photographing. For example, the counter may be located on a cassette or in an apparatus other than the cassette, such as a display apparatus. The counter can be of any kind. However, a counter which increases by 1 at each time of photographing (recording image data) is convenient to use. The counter preferably has reset and preset functions.

"Storing the image data . . . by relating the image data of each image with a photographing menu used at the time of photographing" means to relate the image data and the photographing menu in such a manner that the photographing menu used at the time of obtaining the image data is known when the image data are read from the image memory. In other words, the image data and the photographing menu have a certain relationship (the image data are linked to the photographing menu). To relate the image data and the menu "via a counter value" means the counter value mediates the relationship (link) between the image data and the photographing menu. In other words, the counter value is related to the image data while being related to the photographing menu. The image data and the photographing menu may be linked to each other via another item, as long as the counter value also serves as the mediator. For example, a menu code for identifying the photographing menu may be used so that the image data are related to the counter value while the counter value is related to the menu code related to the photographing menu.

"Storing the image data . . . in the image memory by relating the image data of each image with a photographing" means any manner of storing, as long as the data of each image are stored in the image memory by being related to the photographing menu via the counter value, as has been described above. For example, the counter value may be stored in the image memory (as accompanying information of the image data, for example), together with the image data. Alternatively, the image data may be stored in a memory address related to the counter value. Furthermore, a table relating the counter value with the image data representing each image may be generated so that only-the image data can be stored in the image memory. When the image data are read, the table having been generated is referred to. It is needless to say that the data of the table may be stored in the image memory so that the data can be read thereafter.

It is preferable for the radiation image photographing method of the present invention to relate an identification code for identifying the radiation detection cassette with the counter value. Any method can be used for relating the identification code with the counter value, as long as the cassette used can be identified at the time the image data are read from the image memory.

A radiation image photographing apparatus of the present invention is an apparatus for realizing the above method. In other words, the radiation image photographing apparatus of the present invention uses a radiation detection cassette containing a radiation detector for outputting image data by detecting radiation representing radiation image information obtained by photographing and an image memory for storing the image data output from the radiation detector, and the radiation image photographing apparatus comprises:

means for storing image data representing a plurality of images in the image memory by relating the image data representing each image with a photographing menu used at the time of obtaining the image data, via a counter value for counting how many times photographing has been carried out.

As this means, any means can be used as long as the image data representing each image are related to the photographing menu via the counter value.

For example, the counter value transferred from the cassette may be related to the photographing menu on a display apparatus controlling photographing. Alternatively, the counter value may be managed on the display apparatus in order to relate the counter value with the photographing menu, while the counter value is transferred to the cassette so that the image memory within the cassette stores the image data by relating the counter value having been transferred with the image data. The transfer of the counter value may be carried out by using either a wired or wireless system.

It is preferable for the radiation image photographing apparatus of the present invention to comprise means for relating an identification code for identifying the radiation detection cassette with the counter value.

As the means for relating the identification code with the cassette, any means can be adopted as long as the counter value is related to the identification code so that the cassette used can be identified. For example, the identification code may be recorded in the image memory together with the image data, or the identification code may be referred to when the image data are read.

The radiation detection cassette of the present invention is used in the radiation image photographing method and apparatus described above. In other words, the cassette contains a radiation detector for outputting image data by detecting radiation representing radiation image information obtained by photographing and an image memory for storing the image data output from the radiation detector, and the image memory stores:

the image data representing a plurality of images by relating the image data with a photographing menu used at the time of obtaining the image data representing each image, via a counter value for counting how many times photographing has been carried out.

It is preferable for the image memory to record an identification code for identifying the cassette.

As the radiation detector contained within the radiation detection cassette of the present invention, radiation detectors of various types described above can be used. However, the present invention is not limited to the above example, and any solid-state radiation detector can be used as long as the radiation detector includes solid-state detection devices aligned with each other and each comprising a semiconductor for detecting radiation as a main part thereof.

According to the radiation image photographing method and apparatus and the radiation detection cassette of the present invention, the image data representing each image are stored in the image memory by being related to the photographing menu used at the time of obtaining the image data, via the counter value for counting how many times photographing has been carried out. Therefore, even if an image memory having sufficient capacity to record a plurality of images is used, the photographing menu can be properly related to the image data representing each image. As a result, even if photographing is carried out in an order different from a predetermined order, the relationship between the menu and the image data can be established and the photographing menu can be properly related to actual images represented by the image signals stored in the image memory.

Furthermore, if the identification code for identifying a cassette is related to the counter value, which cassette has been used can be known easily, and the photographing menu can be accurately related to the image data even if a cassette different from a predetermined cassette has been used.

BRIEF DESCRIPTION OF THE DRAWINGS

FIG. 3 is a diagram explaining an operation of the radiation image photographing apparatus using the radiation detection cassette shown in FIG. 1;

FIG. 7 is a diagram explaining an operation of a radiation image photographing apparatus using the radiation detection cassette shown in FIG. 6.

DESCRIPTION OF THE PREFERRED EMBODIMENTS

Hereinafter, embodiments of the present invention will be explained with reference to the accompanying drawings.

Figure 1:
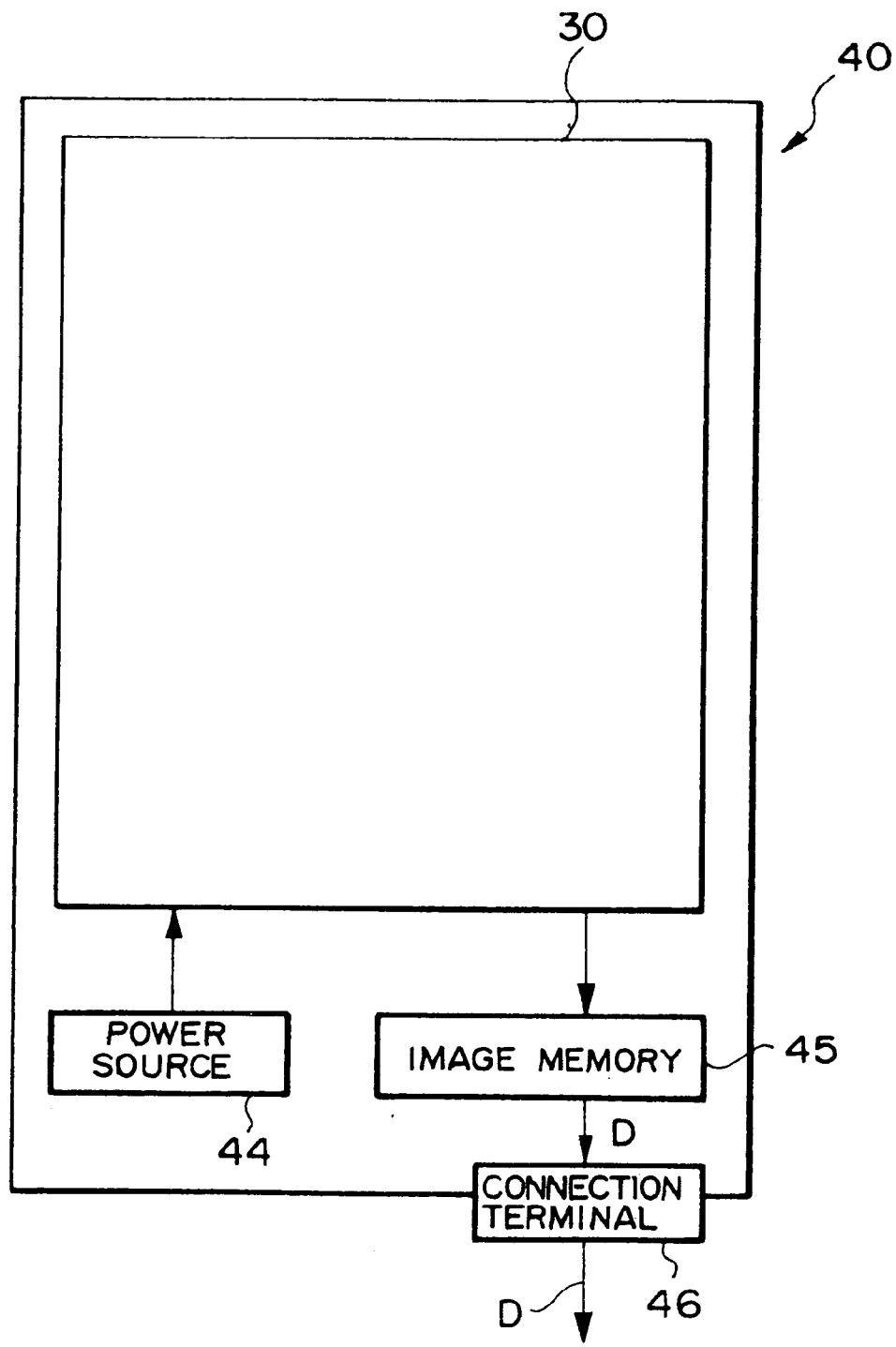
FIG. 1 is a plain view showing an embodiment of a radiation detection cassette of the present invention.
Figure 2:
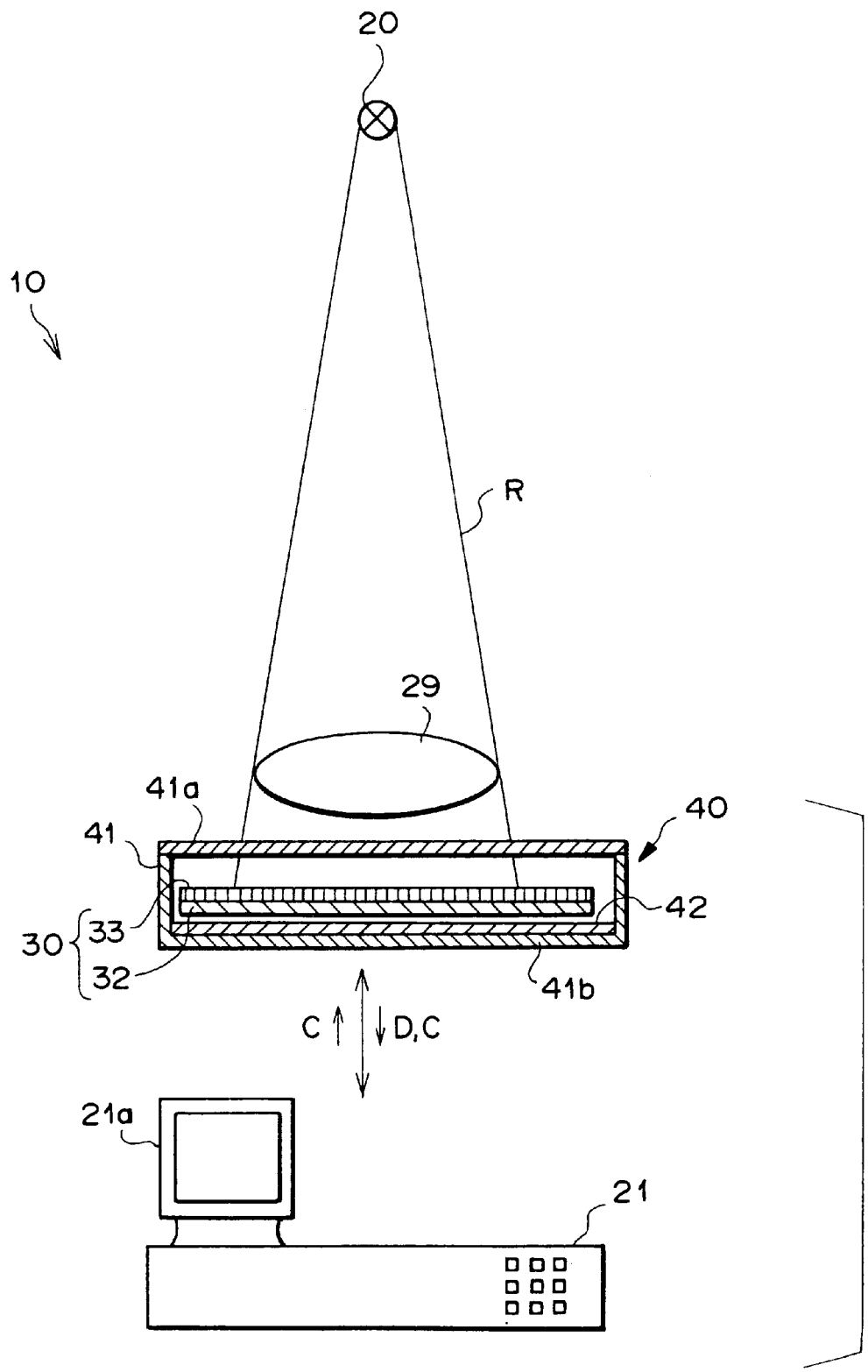
FIG. 2 is an illustration showing a subject and an outline configuration of a radiation image photographing apparatus of the present invention using the radiation detection cassette shown in FIG. 1.

FIG. 1 is a plain view showing an embodiment of a radiation detection cassette of the present invention, and FIG. 2 is an illustration showing a subject and an outline configuration of a radiation image photographing apparatus using the radiation detection cassette of the present invention and realizing a radiation image photographing method of the present invention.

A radiation image photographing apparatus 10 comprises a radiation source 20, a display apparatus 21 (for displaying image and information) controlling photographing, and a radiation detection cassette 40.

The radiation detection cassette 40 is located at a position where radiation R representing information of transmitted radiation penetrating through a subject 29 enters from the radiation source 20 as shown in FIG. 2, and contains a solid-state radiation detector 30 therein.

The radiation detection cassette 40 is connected to the display apparatus 21. A signal processing unit (not shown in FIG. 2) for processing image data is located within the display apparatus 21.

First, configuration and operation of the radiation detection cassette 40 will be explained in detail.

The radiation detection cassette 40 comprises, as shown in FIGS. 1 and 2, an enclosure 41 for containing the radiation detector 30, an image memory 45 connected to the detector 30 and for storing image data D read (output) from the detector 30, a connection terminal 46 connected to the image memory 45 and for outputting the image data D stored in the image memory 45 to the external display apparatus 21, and a power source 44 for driving solid-state detection devices and a reading circuit (both not shown) both forming part of the detector 30. As shown in FIG. 2, a top surface of the cassette enclosure 41 from which the radiation R enters first is a top plate 41a also serving as a grid, and an inner surface of a bottom plate 41b of the enclosure 41, which the radiation R having passed through the detector 30 enters, has a lead layer 42 thereon for backscatter prevention.

As the radiation detector 30 contained in the cassette 40, any solid state detector can be used as long as the detector comprises solid state detection devices aligned with each other and each comprising a semiconductor for radiation detection as a main part thereof.

A counter value C counting how many times photographing has been carried out is transferred from the display apparatus 21 to the cassette 40.

An image memory having sufficient recording capacity for a plurality of images is used as the image memory 45. An image signal is output from the detector 30 every time photographing is carried out and the image signal is digitized by an A/D converter which is not shown. The image data D having been digitized are recorded (stored) in an area of a predetermined address in the image memory 45. The predetermined address does not necessarily have any particular relationship with the counter value C, and any address can be used.

The image data D having been stored in the image memory 45 are transferred to the display apparatus 21 via the connection terminal 46.

In the display apparatus 21, a signal processing unit (not shown) carries out signal processing such as image processing on the image data D and reproduces a radiation image of the subject 29 as a visible image to be used for diagnosis or judgment of necessity of re-photographing.

Various means can be used for reproducing the image. For example, electronic display means such as a CRT or means for recording a radiation image displayed on a CRT or the like by using a video printer or the like can be used. Alternatively, the radiation image of the subject 29 may be recorded in a magnetic tape, an optical disc, or the like.

An operation of the radiation detection cassette 40 will be explained next.

In the radiation detection cassette 40 containing the radiation detector 30 and the image memory 45 described above within the enclosure 41, the image data D of the subject 29 represented by the latent image charge recorded in the detector 30 by photographing are output in time series and stored in the predetermined address of the image memory 45. At this time, the counter value C transferred from the display apparatus 21 is recorded as accompanying information of the image data D in the image memory 45.

The cassette 40 storing the image data D of the subject 29 in the image memory 45 transfers the image data D to the signal processing unit of the display apparatus 21 via the connection terminal 46 connected to the image memory 45.

The signal processing unit reproduces the radiation image of the subject 29 as a visible image after carrying out signal processing such as image processing on the image data D.

As has been described above, according to the radiation detection cassette 40 in this embodiment, it is not necessary to constantly connect the detector 30 to the display apparatus 21 or to the power source 44 via a cable. Therefore, the detector 30 can be transported freely by hand by being contained within the cassette 40, and a degree of freedom of photographing, such as positioning, can be enhanced.

Furthermore, since the image memory having sufficient recording capacity for a plurality of images is used as the image memory 45, output of the image data to the external signal processing unit each time one image is detected is not necessary. The image data corresponding to the plurality of images are output collectively from the image memory 45 to the signal processing unit following establishment of the connection thereto after the images have been detected and stored. Therefore, processing time from signal detection to signal processing can be reduced.

Moreover, by setting a size of the cassette to almost the same size as a cassette used in a conventional radiation photographing system or a radiation image photographing and reproducing system, the cassette 40 can be used as it is for the conventional systems.

The radiation detection cassette 40 of the present invention can adopt a heat insulating layer covering the portion facing the detector. By adopting such a configuration, dark current noise occurring in the detector can be reduced by heat insulation between the detector and the outside thereof.

An operation of the radiation image photographing apparatus 10 using the radiation detection cassette 40 described above and realizing the radiation image photographing method of the present invention will be explained next.

FIG. 3 is a diagram for explaining the operation of the radiation image photographing apparatus 10 using the radiation detection cassette 40. The apparatus 10 generates the counter value C in the display apparatus 21 and the counter value C is related to the photographing menu while being transferred to the cassette 40. In the cassette 40, the transferred counter value C is stored in the image memory 45 together with the image data D. In this manner, the counter value is related to the image data for each image. In other words, the image data D for each image stored in the image memory 45 are related to the photographing menu used upon obtaining the image data, via the counter value C generated in the display apparatus 21. In this manner, when the image data D are read from the image memory 45, the photographing menu used at the time of obtaining the image data can be known by referring to the counter value C. Hereinafter, this operation will be explained in detail.

In the case where radiation photographing is judged to be necessary when a clinician carries out a diagnosis on a patient in a consulting room, the clinician transfers the photographing menu such as patient information (name, age, gender, and the like) and photographing information (a body part to be photographed, a direction of photographing, an image size, and the like) to the display apparatus 21 in a photographing room via a network which is not shown.

The patient to be photographed appears in the photographing room and a photographer (normally a radiologist) determines a photographing condition and an image processing condition according to the photographing menu when the patient's turn comes. The photographer then positions the cassette 40.

The photographer relates the photographing menu used at this time to the counter value C, and transfers the counter value C from the display apparatus 21 to the cassette 40. The photographing menu is related to the counter value C by generating a table relating the menu and the value, for example. It is convenient for the table to be generated automatically by data processing, since the photographing menu has been transferred to the display apparatus 21 via the network. Alternatively, the photographer may generate the table by writing down the counter value C on a document describing the photographing menu, for example.

Photographing is carried out according to the photographing condition having been determined, and the counter value C transferred from the display apparatus 21 is stored as the accompanying information of the image data D in the image memory 45, together with the image data D.

Storing the image data D and relating the counter value C to the photographing menu are repeated in order according to the photographing menu, and the image data for a plurality of images such as images of the lumber vertebra in 6 directions each for several patients are stored in the image memory 45, for example.

In parallel to the processing described above, an identification code for identifying the cassette is stored in the image memory 45. Upon recording the identification code, the code is preferably stored as the accompanying information of the image data D for each image. The identification code may be recorded individually before or after the processing sequence described above.

Figure 4:
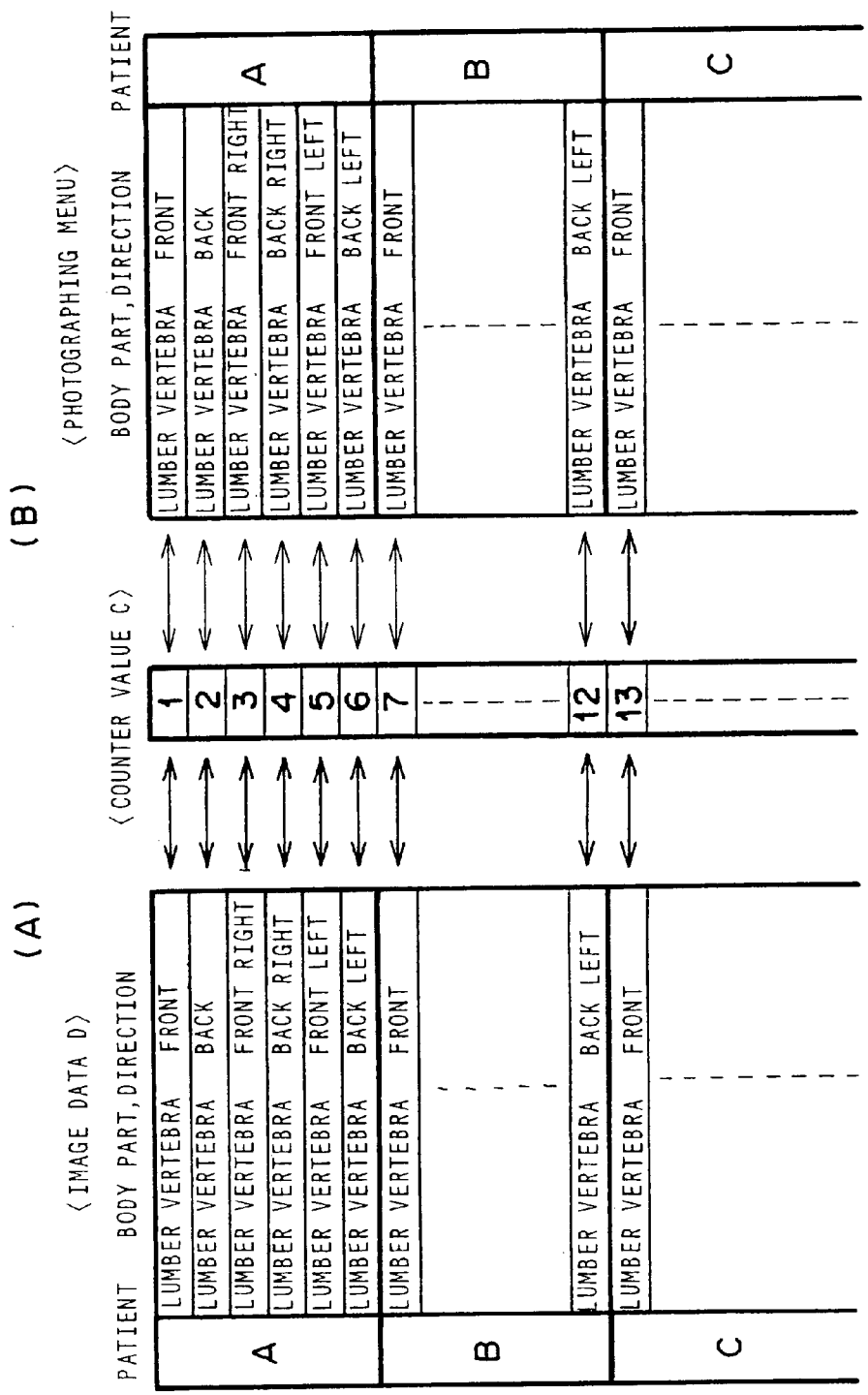
FIG. 4 is a schematic diagram in which the left half (A) shows correspondence between a counter value in an image memory and image data, and the right half (B) shows correspondence between a counter value in a display apparatus and a photographing menu.

FIG. 4 is a diagram showing how the counter value C is related to the image data D in the image memory 45 [FIG. 4(A)] and how the counter value C in the display apparatus 21 is related to the photographing menu [FIG. 4(B)]. As shown in FIG. 4, the image data D are related to the photographing menu via the counter value C.

After the processing sequence described above has been completed, the cassette 40 is connected to a cassette stand (not shown) of the display apparatus 21 and the counter value C, the image data D, and the identification code are read from the image memory 45.

The display apparatus 21 confirms whether or not the identification code of the cassette having been used is the identification code of the cassette to be used, and relates the photographing menu (such as the patient information and the photographing information) to the image data D by finding agreement of the counter value between the photographing menu and the image data D. According to the photographing menu having the same counter value (related to the image data), predetermined image processing is carried out on the image data D for each image and displayed on a display screen 21a of the display apparatus 21. If a flaw is found in the image when the image is examined, re-photographing may be carried out.

A radiologist reads each image having been obtained, and inputs his/her comment in the display apparatus. The image data D and the comment for each patient are then transferred to each clinician of the patient via the network, and used for a diagnosis.

As has been described above, necessity of photographing is judged in a consulting room, and the order in which the patients are to be photographed and the directions of photographing are determined by a clinician. The kind of cassette used for photographing is also determined. The order of photographing and the kind of cassette to be used are all managed as a portion of the photographing menu.

Since the photographing menu is transferred to the photographing room via the network, the image data D can be related to the photographing menu without recording the counter value C as the accompanying information of the image data D in the image memory 45, if the order of photographing is in accordance with the photographing menu.

Figure 5A:
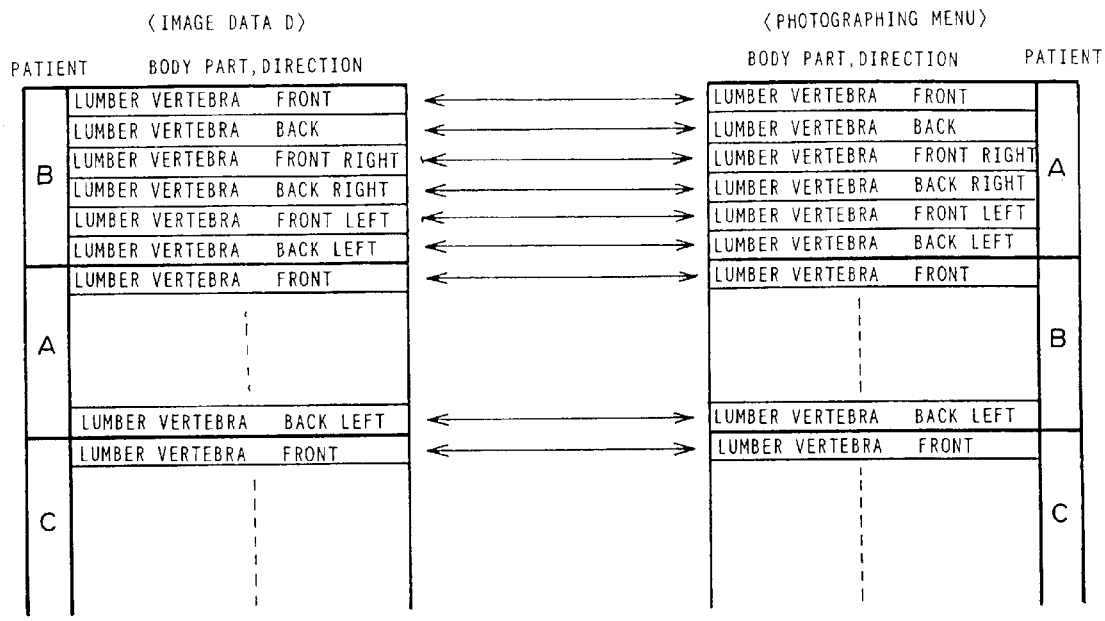
FIGS. 5A and 5B are diagrams showing correspondence between image data and photographing menu when photographing order becomes different from predetermined order in the cases where a counter value relating image data to the photographing menu do not exist [FIG. 5A] and exists [FIG. 5B]

However, when the order is changed, that is, when the order of the patients to be photographed or the order of photographing directions is changed, the image data D cannot be related to the photographing menu unless the counter value C is recorded as the accompanying information of the image data D (that is, unless the counter value is related to the image data D). For example, as shown in FIG. 5A, when the photographing order is swapped between patients A and B, an image of the patient A may be mistaken as an image of the patient B when the image data are read from the image memory 45.

Figure 5B:
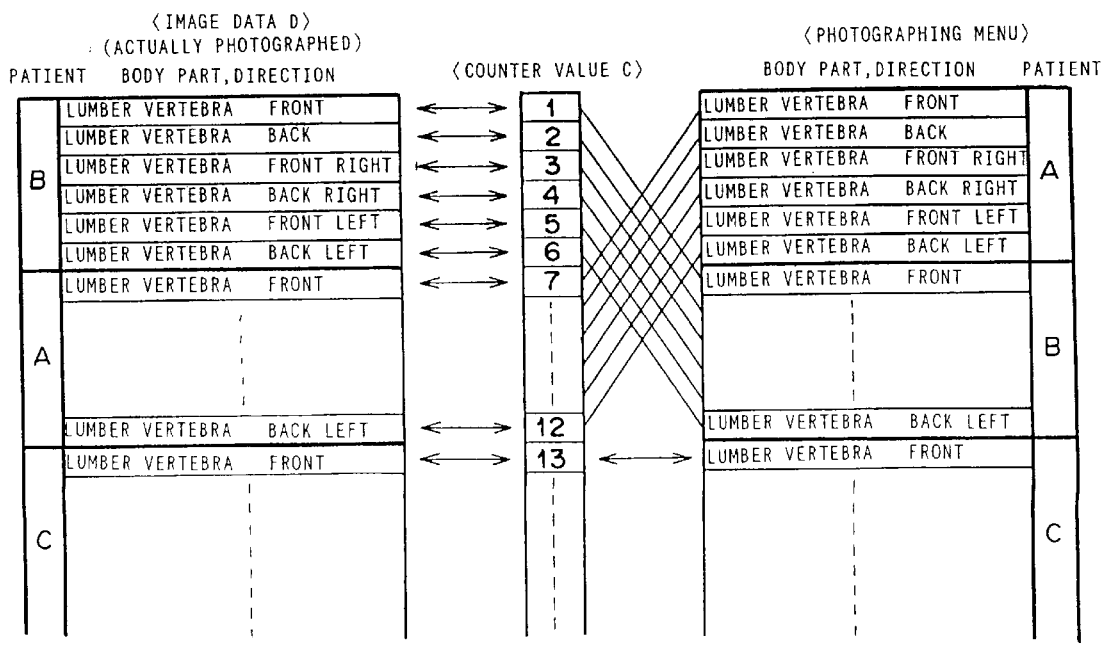

Meanwhile, according to the present invention, since the counter value C is recorded in the image memory 45 as the accompanying information of the image data D, the image data having the counter value 1 can be recognized properly as the image data obtained by photographing the lumber vertebra of the patient B from the front, as shown in FIG. 5B, for example. Therefore, even when the photographing order has been changed, the image data can be properly related to the photographing menu.

Likewise, when the kind of cassette having been used is the same as the kind of cassette in accordance with the photographing menu, the cassette, the image data D, and the photographing menu can be related to each other without recording the identification code in the image memory 45.

However, when the kind of cassette having been used is different from the kind of cassette in accordance with the photographing menu, identical counter values may exist. As a result, image data read from the cassette having a cassette number different from the predetermined number may be mistaken for the desired image data. Therefore, as in the case of the photographing order change described above, the image data D cannot be related to the photographing menu.

Meanwhile, according to the present invention, since the identification code of the cassette is recorded in the image memory 45, which cassette has been used can be known by confirming the cassette with the identification code read from the image memory 45. Therefore, even in the case where the cassette different from the predetermined cassette has been used, the image data D can be related to the photographing menu with certainty.

Figure 6:
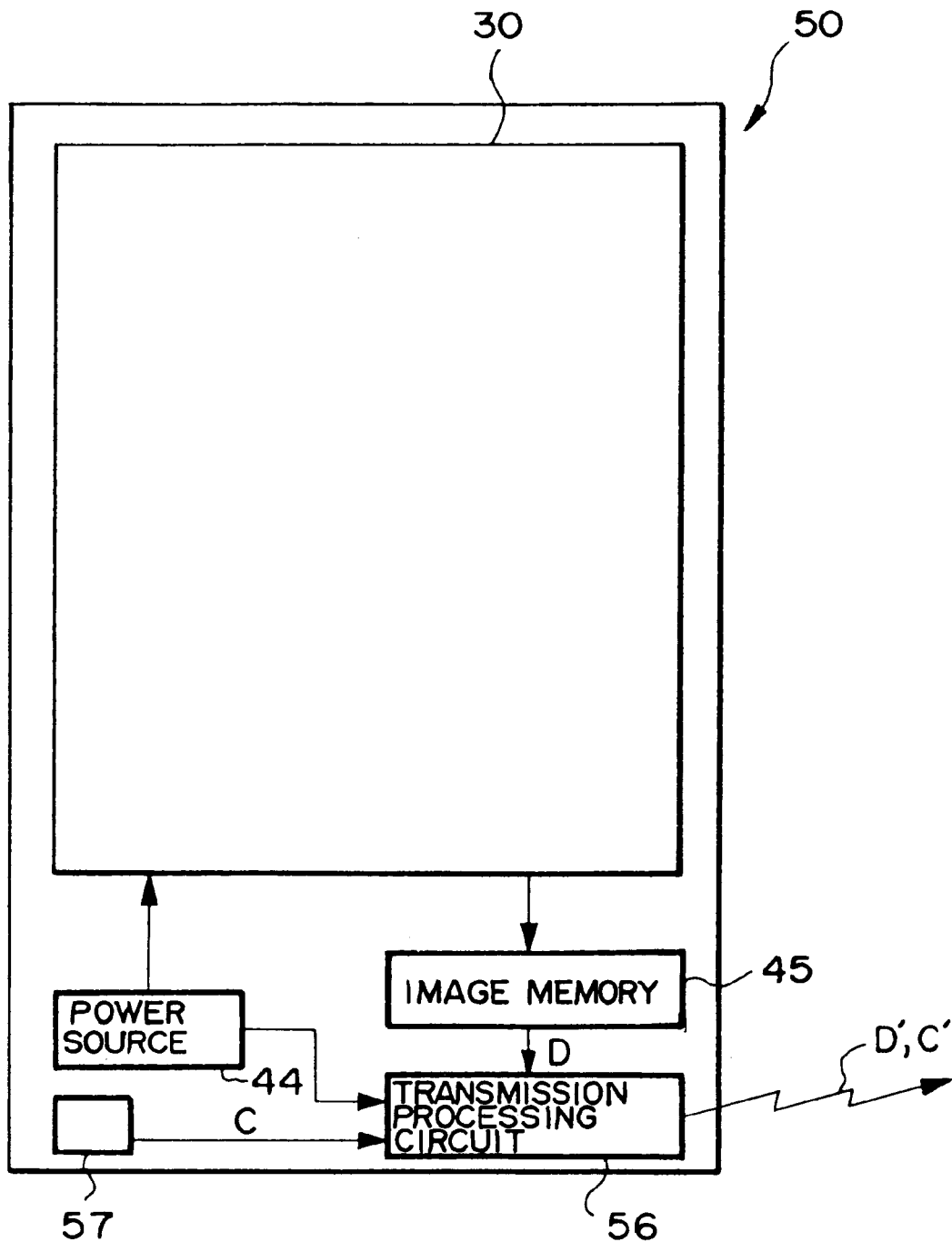
FIG. 6 is a plain view of another embodiment of a radiation detection cassette of the present invention.

FIG. 6 is a plain view showing another embodiment of the radiation detection cassette of the present invention. A cassette 50 shown in FIG. 6 is different from the cassette 40 shown in FIG. 1 in that the cassette 50 comprises a transmission processing circuit 56 for outputting the image data D stored in the image memory 45 by converting the image data D into radio data D', instead of the connection terminal 46 of the cassette 40 shown in FIG. 1. The transmission processing circuit 56 carries out the above operation by receiving energy from the power source 44.

The cassette 50 also comprises a photographing counter 57 for counting how many times photographing has been carried out, and the cassette 50 records the counter value C in the image memory 45 by relating the value with the image data D while transferring the counter value C to the display apparatus 21 by converting the counter value C into radio data D' by using the transmission processing circuit 56.

In the cassette 50, the image data D of the subject 29 represented by the latent image charge recorded in the radiation detector 30 by photographing are output in time series by the same operation as by the cassette 40, and recorded in a predetermined address in the image memory 45.

The image data D and the counter value C stored in the image memory 45 are converted into the radio data D' and C' by the transmission processing circuit 56 connected to the image memory 45, and transferred to the signal processing unit in the display apparatus 21. The signal processing unit receives the radio data D' and C' and carries out signal processing such as image processing thereon.

As has been described above, according to the radiation detection cassette 50 of the present invention, it is unnecessary for the radiation detector 30 to be constantly connected to the external signal processing unit and the power source via a cable, as in the case of the cassette 40 described above. Therefore, the radiation detector can be transported freely by hand by being contained within the cassette and the degree of freedom such as positioning or the like at the time of photographing can be improved.

An operation of a radiation image photographing apparatus 10' using the radiation detection cassette 50 instead of the radiation detection cassette 40 will be explained next.

FIG. 7 is a diagram explaining the operation of the radiation image photographing apparatus 10' using the radiation detection cassette 50. In the radiation image photographing apparatus 10', the counter value C is generated by the cassette 50 so that the counter value C is related to the image data D for each image to be recorded in the image memory 45, while the counter value is converted into the radio data C' and transferred to the display apparatus 21 in order to be related to the photographing menu. In other words, the image data D for each image are related to the photographing menu used at the time of obtaining the image data D via the counter value C generated in the cassette. In this manner, the photographing menu used at the time of obtaining the image data D is known by referring to the counter value C when the image data D are read from the image memory 45. Hereinafter, this operation will be explained in detail.

If a clinician judges that radiation photographing is necessary when he/she carries out a diagnosis on a patient in a consulting room, the patient brings a document describing the photographing menu including the patient information (such as name, age, and gender) and the photographing information (such as a body part to be photographed, a direction of photographing, and an image size) to a photographing room.

A photographer (normally a radiologist) to whom the document is provided by the patient appearing in the photographing room determines a photographing condition and an image processing condition according to the photographing menu, and positions the cassette 50 with respect to the patient.

Photographing is carried out according to the determined photographing condition, and the image data D and the counter value C of the photographing counter 57 as the accompanying information of the image data D obtained by this photographing are stored in the image memory 45. At this time, the cassette 50 converts the counter value C of the photographing counter 57 into the radio data C' and transfers the radio data C', to the display apparatus 21. The display apparatus 21 receives the radio data C' and relates the photographing menu with the counter value C based on the radio data C'. The counter value is related to the menu by using a table generated therefor, for example. This table is generated by the photographer by writing down the counter value C of the photographing counter 57 of the cassette 50 on the document describing the photographing menu (such as the patient information and the photographing information) placed on the display apparatus 21. In this manner, the photographing menu can be related to the counter value C. Alternatively, the photographing menu may be input to the display apparatus 21 in advance so that the table relating the radio data C' (that is, the counter value C) to the photographing menu can be generated automatically by data processing.

Storing the image data D and relating the counter value C to the photographing menu are repeated in order according to the photographing menu, and the image data for a plurality of images such as images of the lumber vertebra in 6 directions each for several patients are stored in the image memory 45, for example.

In parallel to the processing described above, the identification code for identifying the cassette is stored in the image memory 45. Upon recording the identification code, the code is preferably stored as the accompanying information of the image data D for each image. The identification code may be recorded individually before or after the series of processing described above.

As has been described above, the image data D are related to the photographing menu via the counter value C, as in the case shown by FIG. 4.

After the processing sequence described above has been completed, the cassette 50 is connected to a cassette stand (not shown) of the display apparatus 21 and the counter value C, the image data D, and the identification code are read from the image memory 45.

The display apparatus 21 confirms whether or not the identification code of the cassette having been used is the identification code of the cassette to be used, and relates the photographing menu (such as the patient information and the photographing information) to the image data D by finding agreement of the counter value between the photographing menu and the image data D. According to the photographing menu having the same counter value (related to the image data), predetermined image processing is carried out on the image data D for each image and displayed on the display screen 21a of the display apparatus 21.

A radiologist reads each image having been obtained, and obtains a film image by outputting the image data to a printer (not shown) connected to the display apparatus 21, if the image has been judged to be appropriate. If a flaw is found in the image when the image is examined, re-photographing may be carried out.

The output film is then brought to the clinician, and used for image reading and diagnosis.

Therefore, in the radiation image photographing apparatus 10' using the radiation detection cassette 50 of this embodiment, the image data are related to the photographing menu used at the time of obtaining the image data via the counter value C and stored in the image memory. Therefore, as in the radiation image photographing apparatus 10 using the cassette 40, the image data can be properly related to the photographing menu when read from the image memory 45. Furthermore, even if the cassette according to the photographing menu is not used, the data can be related to the menu with certainty.

In the above embodiments, the counter value is stored in the image memory as the accompanying information of the image data D. However, the present invention is not limited to the above example. Any apparatus which can relate the image data to the photographing menu via the counter value can be used, and any manner of storing the image data in the image memory can be adopted as long as the image data can be related to the photographing menu.

For example, the image data for each image may be stored in a memory address related to the counter value. More specifically, the address of the image data corresponding to the counter value is determined in advance, and only the image data are stored in the address corresponding to the counter value. When the image data are read from the image memory, the image data are related to the photographing menu by matching up which address the image data have been read from (that is, the counter value represented by the address) to the counter value related to the photographing menu. "Which address the image data have been read from" can be known by predetermining the order of reading the image data.

Even if the address to store the image data is not determined in advance, the image data can be related to the photographing menu by generating a table relating the counter value to the image data for each image and by storing only the image data in the image memory. The data of the table may be stored in the image memory. More specifically, an address table describing which address the image data corresponding to the counter value have been stored in is generated, and the image data can be related to the photographing menu upon reading of the image data from the image memory by referring to the address table to find agreement between the counter values of the address and the photographing menu.

In the above explanation, the identification code for identifying the cassette is stored in the image memory together with the image data. However, the present invention is not limited to the above example, and any means can be used as long as the counter value is related to the identification code so that the cassette used can be known. For example, the identification code may be referred to when the image data are read from the image memory, or the identification code may be transferred to the display apparatus together with the image data.

What is claimed is:

1. A radiation image photographing method using a radiation detection cassette containing a solid-state radiation detector for outputting image data by detecting radiation representing radiation image information obtained by photographing and an image memory for storing the image data output from the radiation detector, the radiation image photographing method comprising the step of:

storing the image data representing a plurality of images in the image memory by relating the image data of each image with a photographing menu used at the time of obtaining the image data, via a counter value for counting exposures.

2. A radiation image photographing method as claimed in claim 1, wherein the counter value is recorded in the image memory together with the image data.

3. A radiation image photographing method as claimed in claim 1, wherein the image data for each image are recorded in a memory address corresponding to the counter value.

4. A radiation image photographing method as claimed in any one of claims 1 to 3, wherein an identification code for identifying the radiation detection cassette is related to the counter value.

5. The method of claim 1, further comprising connecting the radiation detection cassette to a processing terminal, and transferring the counter value from the terminal to the image memory on each exposure.

6. The method of claim 1, wherein the counter value corresponds to an incremental change value for each exposure taken.

7. The method of claim 6, further comprising storing a table correlating the photographing menu, the counter value and image data of each image.

8. The method of claim 7, wherein storing the table further comprises storing an identification code for identifying the radiation detection cassette in correlation with each counter value.

9. The method of claim 6, wherein the incremental change is one.

10. A radiation image photographing apparatus using a radiation detection cassette containing a solid-state radiation detector for outputting image data by detecting radiation representing radiation image information obtained by photographing and an image memory for storing the image data output from the radiation detector, the radiation image photographing apparatus comprising:

means for storing image data representing a plurality of images in the image memory by relating the image data representing each image with a photographing menu used at the time of obtaining the image data, via a counter value for counting exposures.

11. A radiation image photographing apparatus as claimed in claim 10, further comprising means for relating an identification code for identifying the radiation detection cassette with the counter value.

12. The apparatus of claim 10, further comprising a terminal connected to the radiation detection cassette, said terminal transferring the counter value to the image memory on each exposure.

13. The apparatus of claim 12, wherein said terminal stores a table correlating the photographing menu, the counter value and image data of each image.

14. The apparatus of claim 13, wherein the table further correlates an identification code for identifying the radiation detection cassette with each counter value.

15. The apparatus of claim 10, wherein the counter value comprises an incremental change value for each exposure taken.

16. The apparatus of claim 15, wherein the incremental change is one.

17. A radiation detection cassette containing a solid-state radiation detector for outputting image data by detecting radiation representing radiation image information obtained by photographing and an image memory for storing the image data output from the radiation detector, the image memory storing:

the image data representing a plurality of images by relating the image data with a photographing menu used at the time of obtaining the image data, via a counter value for counting exposures.

18. The radiation detection cassette of claim 17, further comprising a counter for providing the counter value to the image memory on each exposure.

19. A radiation detection cassette as claimed in claim 17, wherein the image memory stores the image data together with the counter value at the time of photographing.

20. A radiation detection cassette as claimed in claim 17, wherein the image memory stores the image data in a memory address corresponding to the counter value at the time of photographing.

* * * * *